United States Patent [19]
Pratt et al.

[11] Patent Number: 5,315,505
[45] Date of Patent: May 24, 1994

[54] METHOD AND SYSTEM FOR PROVIDING ANIMAL HEALTH HISTORIES AND TRACKING INVENTORY OF DRUGS

[75] Inventors: William C. Pratt, Canyon; William D. McKillip, Amarillo, both of Tex.

[73] Assignee: Micro Chemical, Inc., Amarillo, Tex.

[21] Appl. No.: 827,843

[22] Filed: Jan. 29, 1992

Related U.S. Application Data

[63] Continuation of Ser. No. 457,338, Dec. 27, 1989, abandoned, which is a continuation of Ser. No. 85,073, Aug. 12, 1987, abandoned.

[51] Int. Cl.$^5$ ............................................. G06F 15/42
[52] U.S. Cl. ............................................. 364/413.01
[58] Field of Search ................................. 364/413.01

[56] References Cited

U.S. PATENT DOCUMENTS

| | | | |
|---|---|---|---|
| 4,604,847 | 8/1986 | Moulding, Jr. et al. | 53/75 |
| 4,617,876 | 10/1986 | Hayes | 119/155 |
| 4,686,624 | 8/1987 | Blum et al. | 364/415 |
| 4,712,511 | 12/1987 | Zamzow et al. | 119/51 R |

OTHER PUBLICATIONS

Shapiro, A., "SCAMP . . . ", *Proc Joint Conf. Soc. for Computer Medicine Soc. for Advanced Medical Systems*, 1981, R 858.A2 C6, pp. 51–54.

McEllhiney, R., "Micro Systems", *Feed Management*, vol. 38, No. 3, Mar. 1985, pp. 54–58.

*Primary Examiner*—Stephen M. Baker
*Attorney, Agent, or Firm*—Klarquist Sparkman Campbell Leigh & Whinston

[57] ABSTRACT

A method and system for providing improved drug treatment to selected animals in a retained group. Through the use of a computer system, an operator is immediately provided with the health and drug treatment history of an animal to be treated by identifying the animal. With this information and a diagnosis of the animal's health condition, a drug treatment is chosen. The diagnosis and treatment are entered into the computer system to update the animal's health and treatment history. If a drug treatment has a withdrawal time which requires the animal to remain in the group for a time after treatment, a release date is calculated. If a dosage of a drug treatment is weight-dependent, the weight of the animal is obtained and the proper dosage for the animal is calculated.

70 Claims, 9 Drawing Sheets

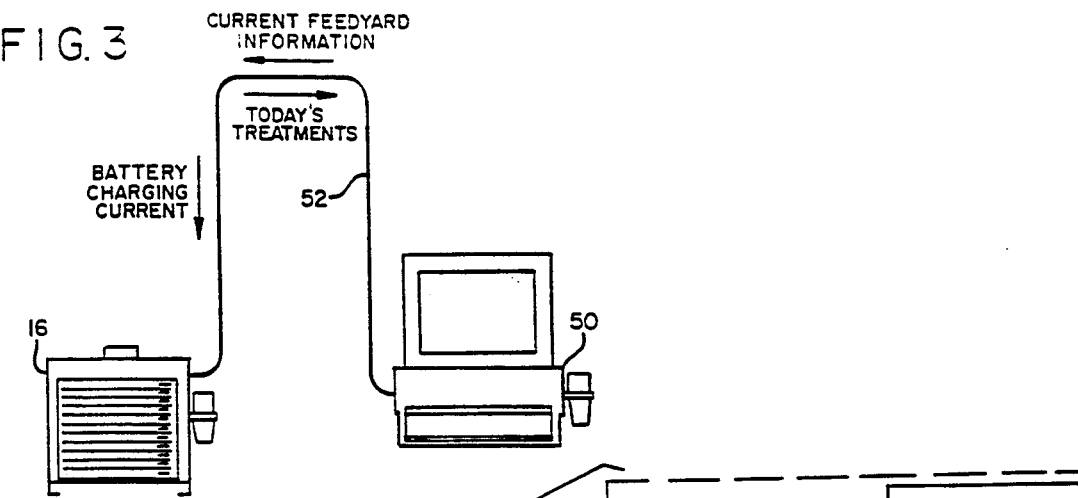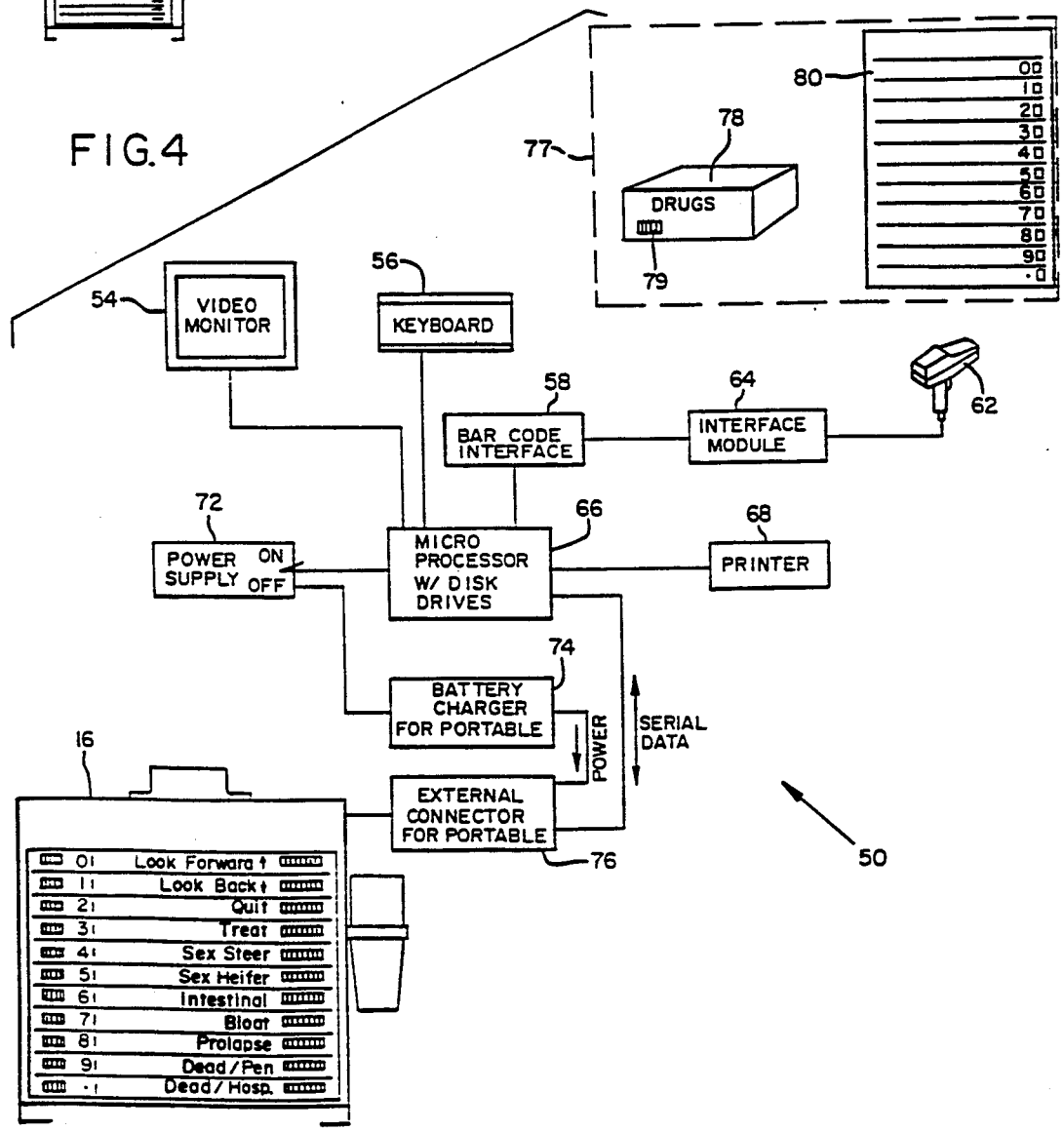

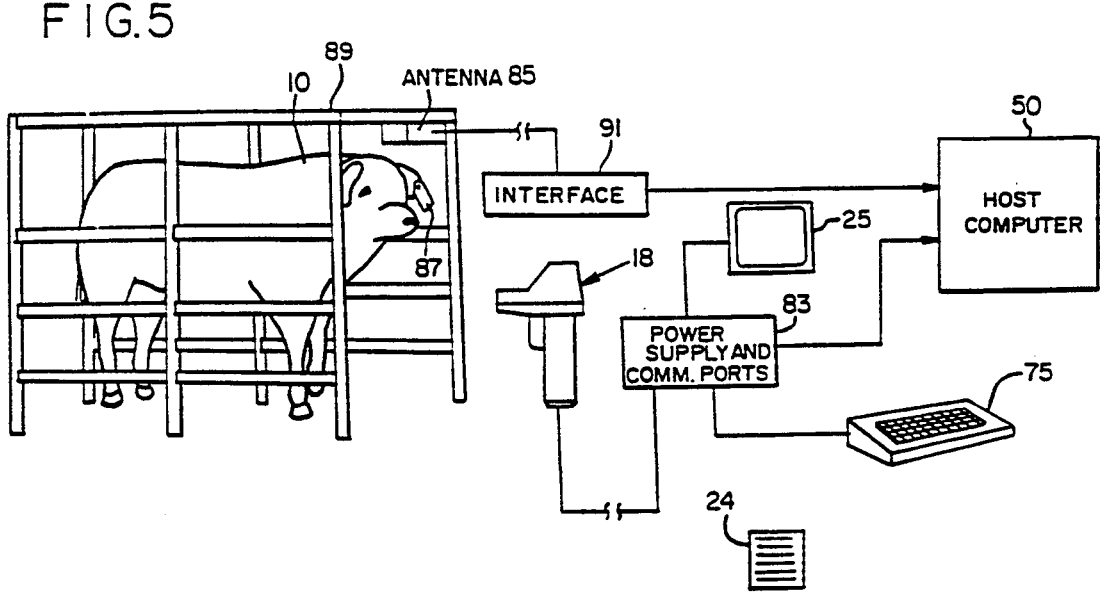

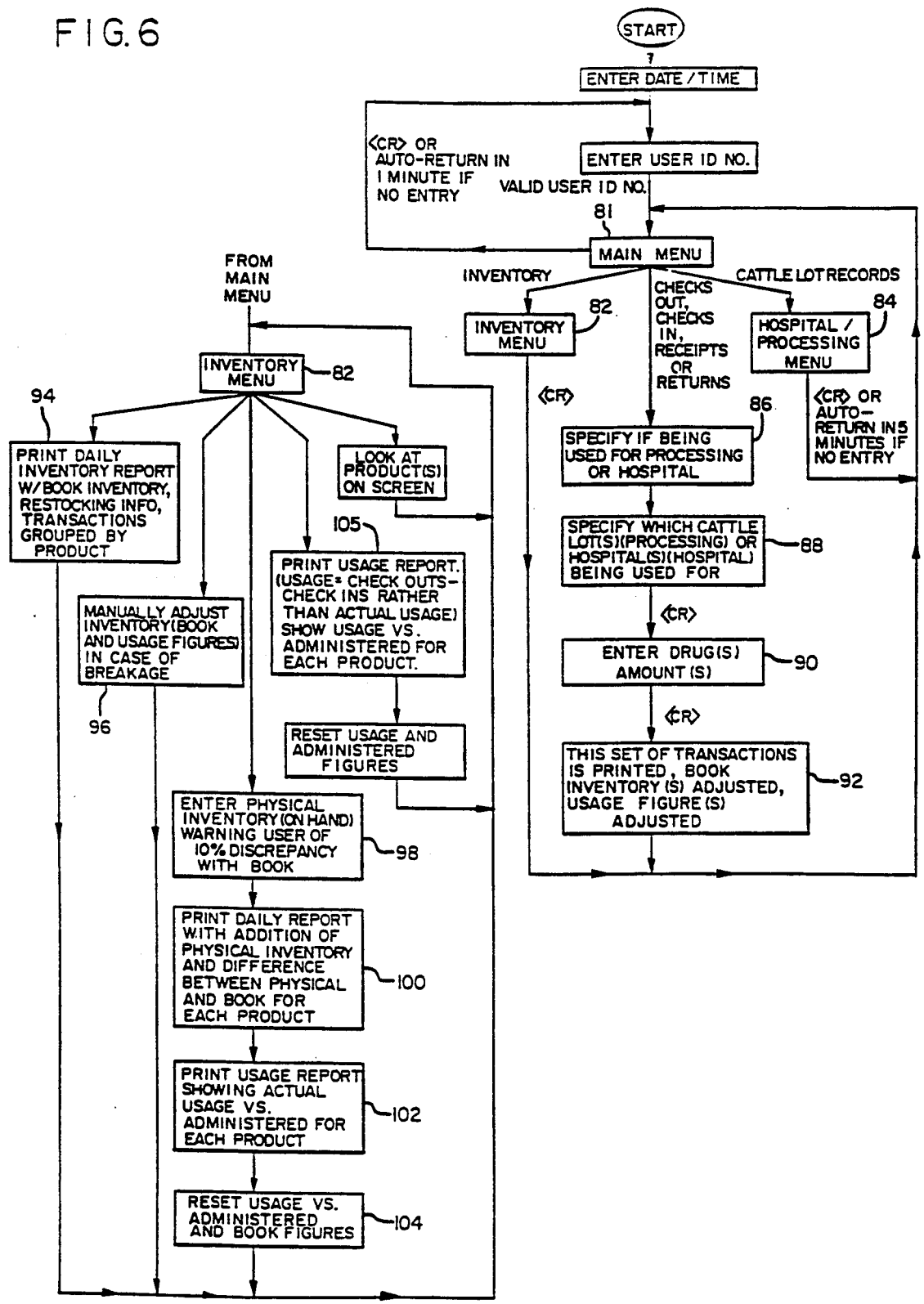

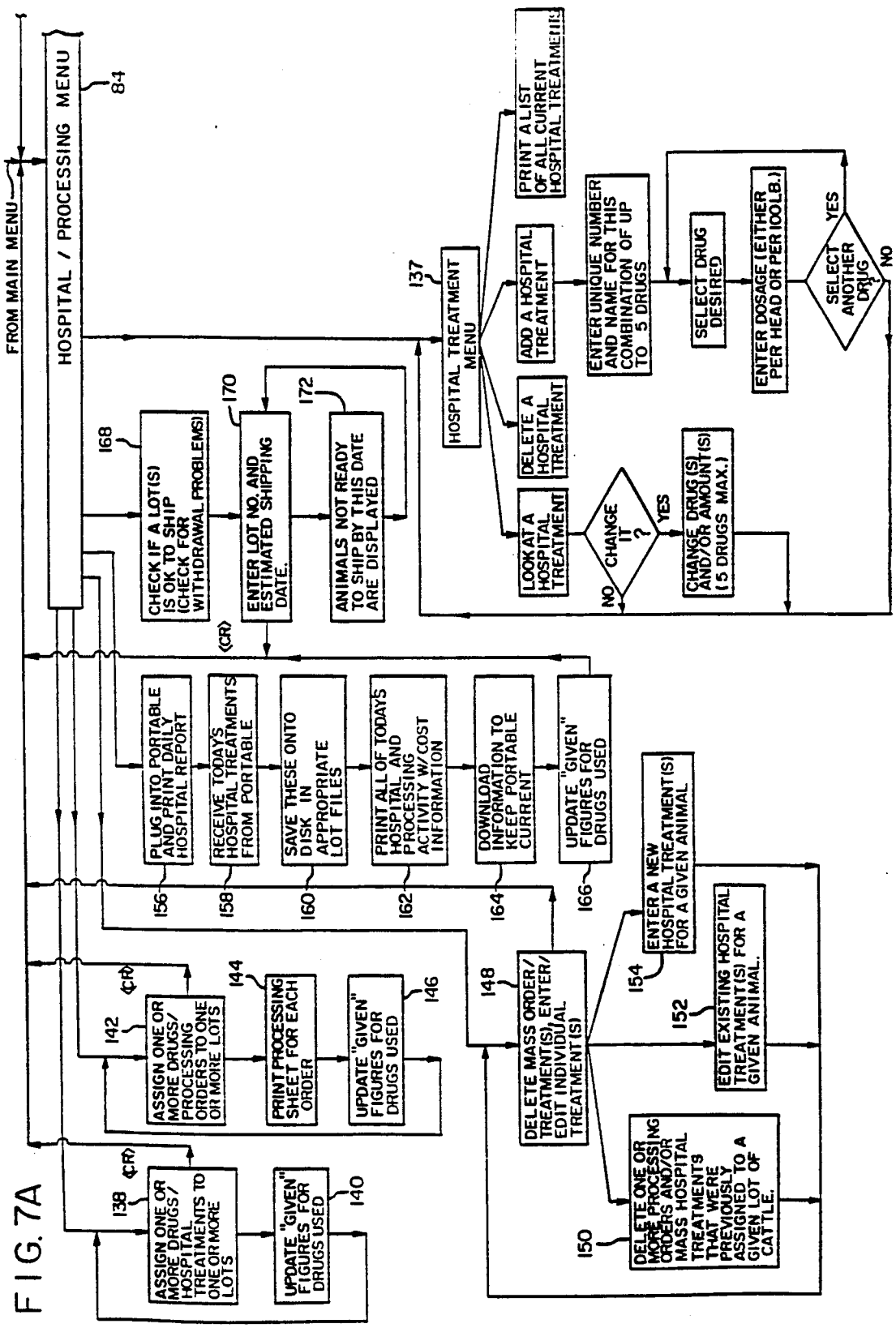

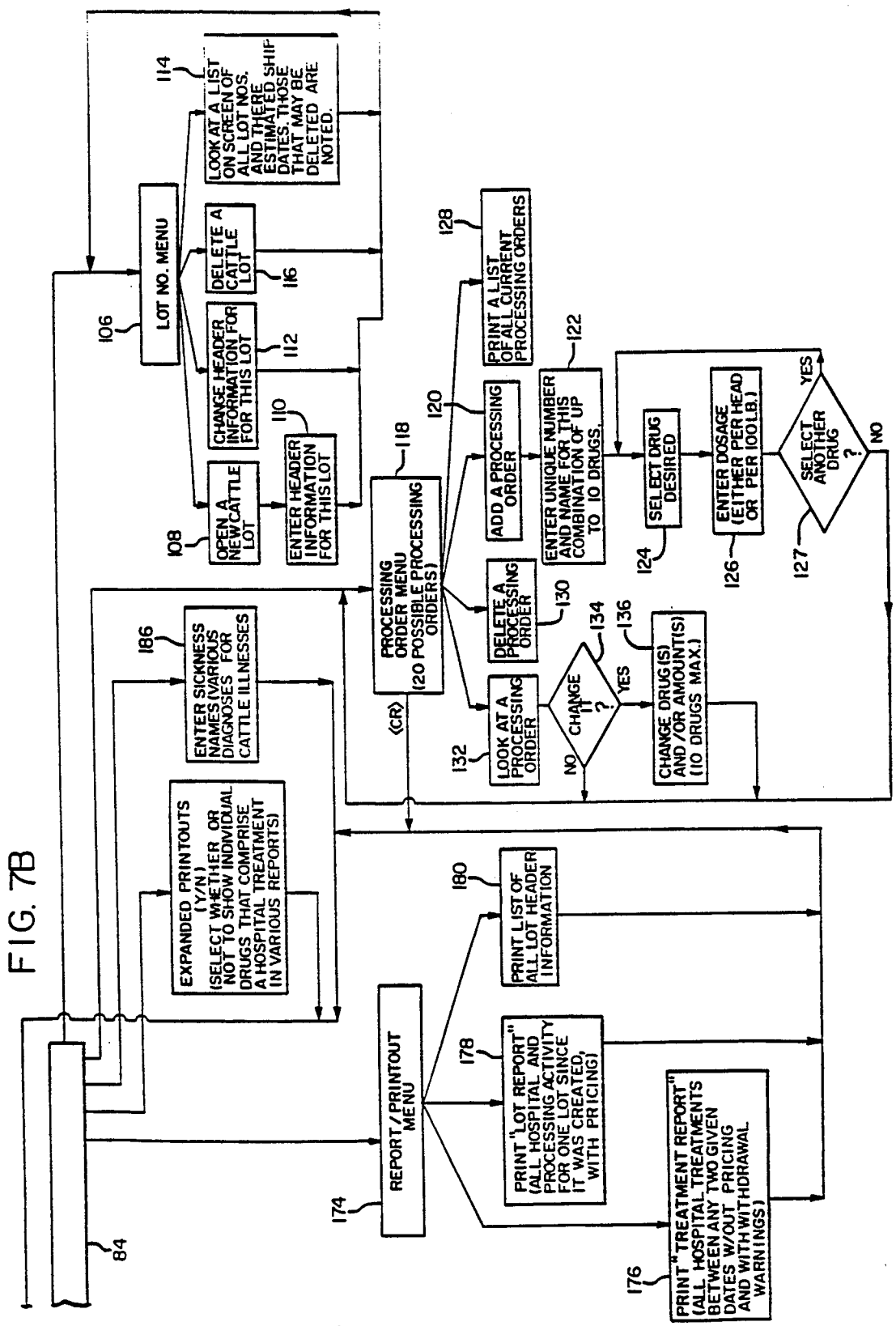

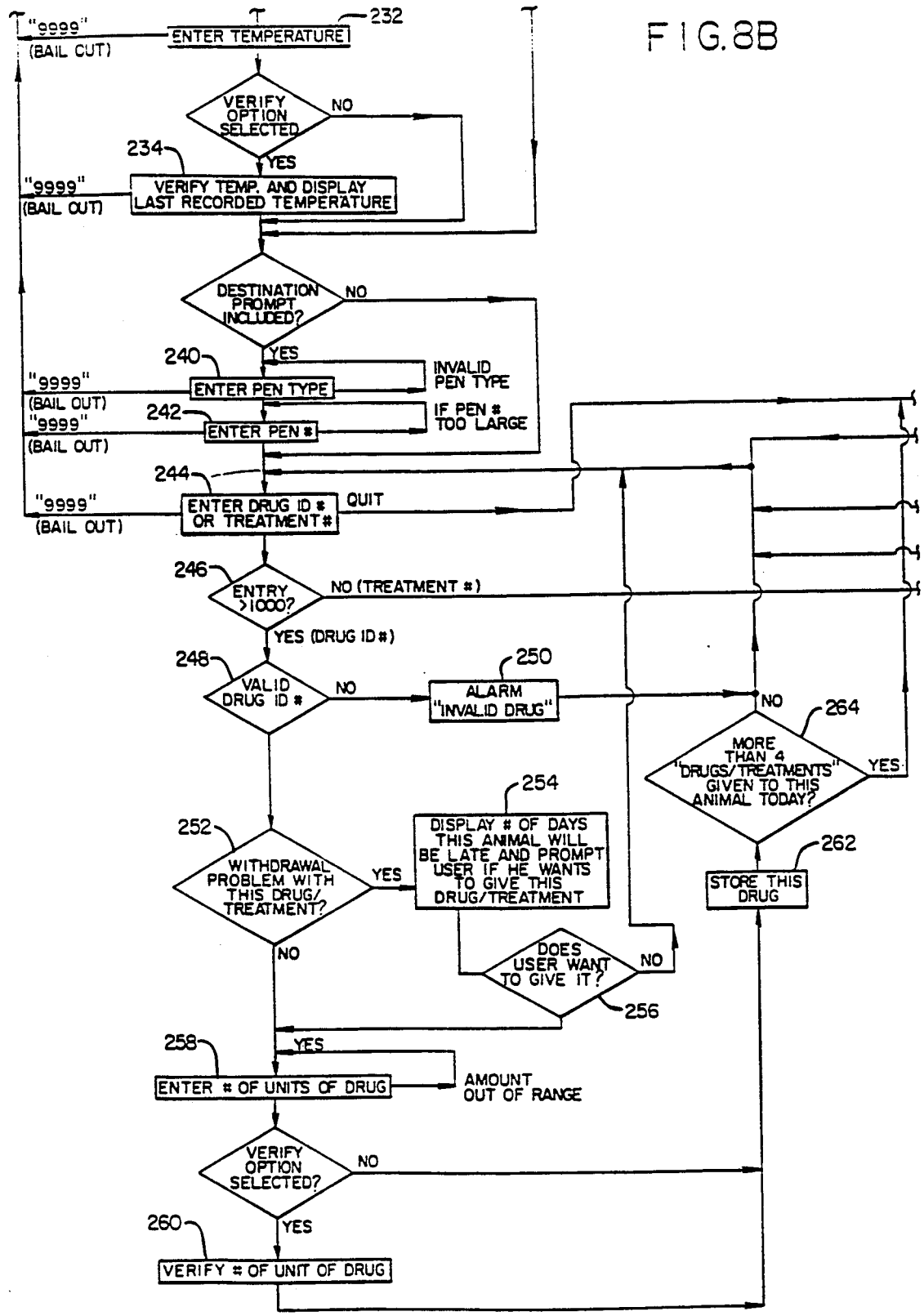

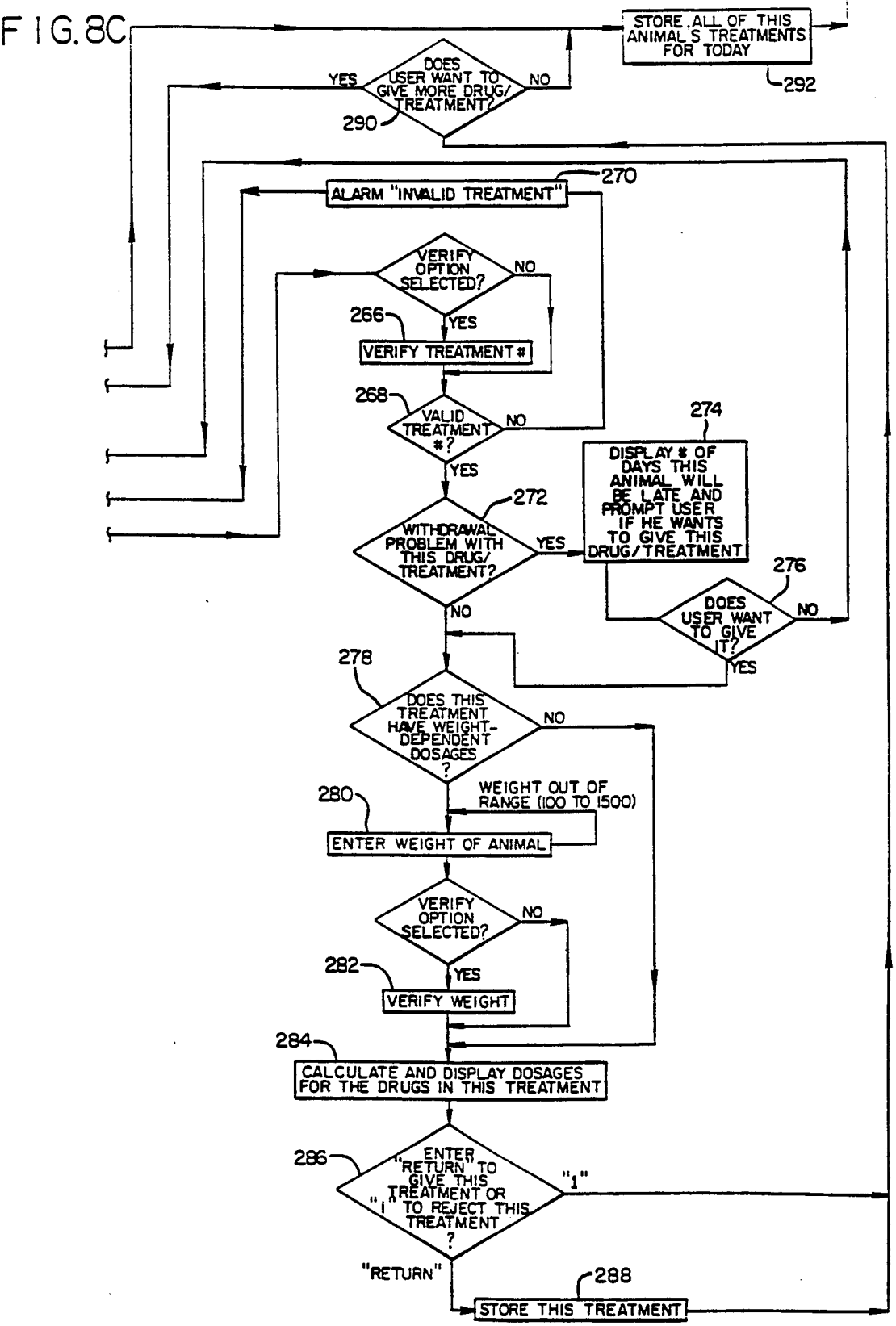

METHOD AND SYSTEM FOR PROVIDING ANIMAL HEALTH HISTORIES AND TRACKING INVENTORY OF DRUGS

This application is a continuation of application Ser. No. 07/457,388, filed on Dec. 27, 1989 now abandoned, which is a continuation of application Ser. No. 07/085,073, filed Aug. 12, 1987, abandoned.

BACKGROUND OF THE INVENTION

This invention relates generally to systems for providing individual health histories of animals, for example, in a cattle feedlot operation. More particularly, this invention relates to such a system wherein the identity of each animal and data representing the physical condition and treatment administered to each animal is recorded, made available at the animal's location, and accumulated with earlier data to provide an up-to-date health history of each animal.

Large scale cattle feedlot operations are commonly employed to feed cattle prior to slaughter. Typically, the cattle of a particular owner are identified by a lot number for keeping track of the goods and services provided for the cattle while in the care of the feedlot. Each individual head is further identified with a unique number such as by tag for keeping track of individual treatments required, such as drugs dispensed for each particular sickness, and for monitoring the physical condition of each animal. Through these identifying numbers, the feedlot operation can maintain a health history for each animal in each lot and charge the cattle owner for feed, drugs, and services provided for each head.

This system, although simple to implement, is slow and fraught with error because of the manual effort required to gather and record the data. Typically, data is manually recorded twice. At an animal hospital on the feedlot, cattle are observed and treated if necessary. An operator records in writing the physical condition of each animal, any observed sickness, and the drug treatment administered. This written record is then transferred to a clerk to be entered into a cumulative history. Both recordings are subject to error. Compounding the problem is the the potential for illegible entries, incomplete entries, and lost entries. For example, often cold, adverse weather conditions at a feedlot make it difficult for an operator to grip the pen for writing and also interfere with the flow of ink through the instrument. Moreover, the manual recording and rerecording are lengthy and consequently the cumulative health history is often several days out of date.

These problems associated with manual entry of data are well known, and attempts have been made to minimize the errors in several aspects of feedlot operations. For example, U.S. Pat. No. 4,288,856 to Linseth discloses an apparatus for separately feeding animals which have not gained sufficient weight. The Linseth apparatus is adapted to weigh each animal as it is walked through a weigh station. An operator reads the identification number that appears on an ear tag of the animal and enters the number into a keyboard connected to a computer. The animal is then weighed and the amount entered into the computer. The computer has stored within its memory different weight ranges for cattle, which the computer compares with the weight of the animal weighed. Each range is related to a gate that leads to a different feeding pen. The computer determines the weight range in which the animals lies and opens the appropriate gate to direct the animal to the desired feeding pen. The procedure is then repeated for reevaluation of the animal after a period of feeding. The Linseth apparatus, however, still requires manual entry of information and lacks any means for creating and displaying at the animal's location a cumulative history of the animal's physical condition and treatment administered.

Other apparatus have addressed individual monitoring of an animal's consumption. U.S. Pat. No. 4,461,240 to Ostler, for example, discloses a monitoring apparatus that dispenses a preselected amount of feed to a cow identified by a transmitter around its neck. The feeding station includes a receiver-transmitter in communication with a computer that has stored within its memory a feeding schedule for the animal. The computer determines how much feed is to be dispensed to each animal individually. The operator can thereby control how much each animal eats and monitor if in fact the prescribed amount of food is consumed. But the apparatus is limited in its ability to monitor and control the feeding of cattle.

U.S. Pat. No. 4,409,950 to Byrne et al. similarly discloses an animal food consumption monitor. Each animal bears a tag that includes a miniature transmitter which transmits a signal identifying the animal. The feed station for the animal includes a receiver for identifying the animal before it begins consuming feed. With the animal identified, the food in the station hopper is weighed before and then after the animal feeds to determine the amount consumed. The data on the amount and type of food consumed is then stored for later retrieval. The Byrne monitor, like the Ostler apparatus, identifies the animal without manual effort. But, again, it provides no on-site, up-to-date history of the animal's health.

Although the apparatus described above and others in the prior art offer some improvements in feedlot operations, they do not address the problem of maintaining up-to-date health histories of the physical condition and the drug treatment of the animals. Such histories are critical in determining the progress of a sick animal as well as in keeping track of the cost of drugs for each animal. The manual method is thus still preferred for this purpose.

SUMMARY OF THE INVENTION

An object, therefore, of the invention is to provide an improved method and system for treating animals.

Another object of the invention is to provide such a system which is portable to the animals' location.

Still another object of the invention is to provide such a system that automates treatment.

Yet another object of the invention is to provide such a system that provides at the animals' location up-to-date health histories for each animal observed and treated.

Yet another object of the invention is to provide such a system that compares the net amount of drugs taken for treatment from a drug inventory against the amount of drugs actually administered from the inventory to determine the difference in amounts.

To achieve these objects, a method according to the invention provides drug treatment to selected individual animals in a group of retained animals. From the group, individual animals are selected and removed to a drug treatment location for specific treatments.

The steps of the method include identifying an animal in need of treatment and moving the animal to the drug treatment location. An operator then enters the animal's identity into a computer system and receives in response the animal's health and treatment history, if any. The health condition is diagnosed and entered into the computer system to update the animal's health history. From an evaluation of the animal's health and treatment history and diagnosed condition, the operator selects a drug treatment. This drug treatment is entered into the computer system to update the animal's drug treatment history.

If a selected drug treatment requires a withdrawal date, a release date is calculated for the animal based on the treatment date.

If the dosage of a selected drug treatment is weight dependent, the animal's weight is obtained and the proper dosage for the animal is calculated.

A preferred way for carrying out the method is with a computer system. A data entry terminal at the drug treatment location allows for ease of data entry, while a computer performs the steps of providing and calculating described above. The computer may be located away from the drug treatment location.

The foregoing and other objects, features, and advantages of the invention will become more apparent from the following detailed description of a preferred embodiment which proceeds with reference to the accompanying drawings.

BRIEF DESCRIPTION OF THE DRAWINGS

FIG. 3 is an illustration of the portable hospital unit in communication with a host computer included in the system.

FIG. 4 is a schematic diagram of the animal health computer of FIG. 3.

FIG. 5 is a schematic diagram of a second embodiment of the system according to the invention.

FIG. 6 is a flowchart illustrating the programming of the host computer.

FIG. 7A is a flowchart illustrating in more detail a portion of the hospital/processing menu within the programming of the host computer.

FIG. 7B is a flowchart illustrating in more detail a second portion of the hospital/processing menu within the programming of the host computer.

FIG. 8B is a flowchart illustrating a second portion of the programming of the portable unit.

FIG. 8C is a flowchart illustrating a third portion of the programming of the portable unit.

DETAILED DESCRIPTION

The System—First Embodiment

Figure 1:
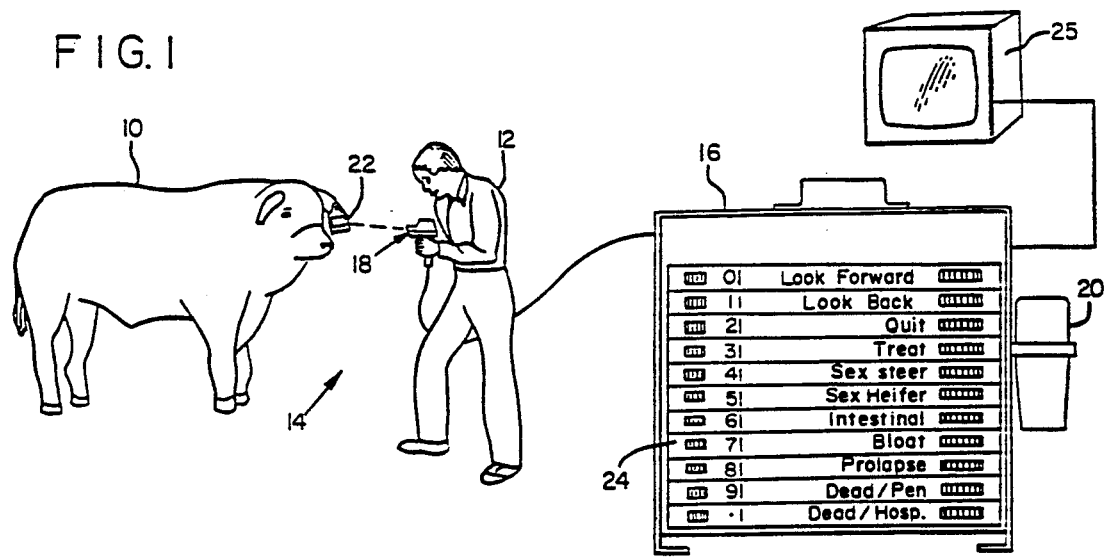
FIG. 1 is an illustration of a portable hospital unit included in a first embodiment of a system according to the invention.

Referring now to FIG. 1, there is shown an animal 10 and an operator 12 in an area of a cattle feedlot referred to as an animal hospital 14. An animal 10 may be brought to the hospital 14 for a check on its physical condition, for treatments that are administered to all animals in a particular lot, and if an animal is to be individually treated for sickness. Typically, the animal hospital 14 includes a cattle chute and a head gate (not shown) for holding the animal stationary while its weight and temperature are checked and any drugs are administered.

As indicated in FIG. 1, the system of the invention in this embodiment includes a portable hospital unit 16 that can be transported to the hospital 14 for use by the operator 12. This portability enables the operator to care for cattle with a single unit at several hospitals located around the feedlot rather than at a single hospital to which all cattle must be directed. Coupled to the portable unit 16 is a means for entering data into the unit such as an optical character reader, which in this first embodiment comprises a portable bar code scanner 18 available from a number of sources including the MSI Data Corporation under the name SYMBOLTEC LS8100. The scanner 18, which is stored in a holster 20 mounted to a side of the unit 16, is adapted to read indicia means such as an ear tag 22 bearing optical characters such as a bar code for uniquely identifying each animal. Rather than having to write down the animal's identifying number on a sheet, therefore, the operator 12 need only scan the ear tag 22 and the identifying number is electronically read and accurately recorded within the unit 16. The portable unit also includes a character menu sheet 24 that bears optical characters such as bar codes corresponding to treatment data comprising the observed physical condition of the animal as well as drug treatments that may be administered. The sheet 24 is mounted behind a clear plastic door of the unit 16 and includes bar codes on the sheet's left and right margins. The bar codes on the left margin are for entering identification numbers of drugs, numerical quantities, and menu selection steps during program execution. The bar codes on the right margin are for entering sickness codes, sex of the animal, and commands for scrolling through the prior health history, for entering data and for quitting after observation or treatment is concluded. The operator can thus enter the identity of the animal and treatment data by simply scanning the menu sheet 24 with the scanner 18. The treatment data is recorded along with the animal's identifying number within the unit 16. Visual feedback to the operator 12 of the prior health history and the data just entered is provided by a display device such as video monitor 25. The monitor 25 also displays the program prompts provided to the operator 12 by the unit 16 for entering the data, as will be described in detail hereafter.

Figure 2:
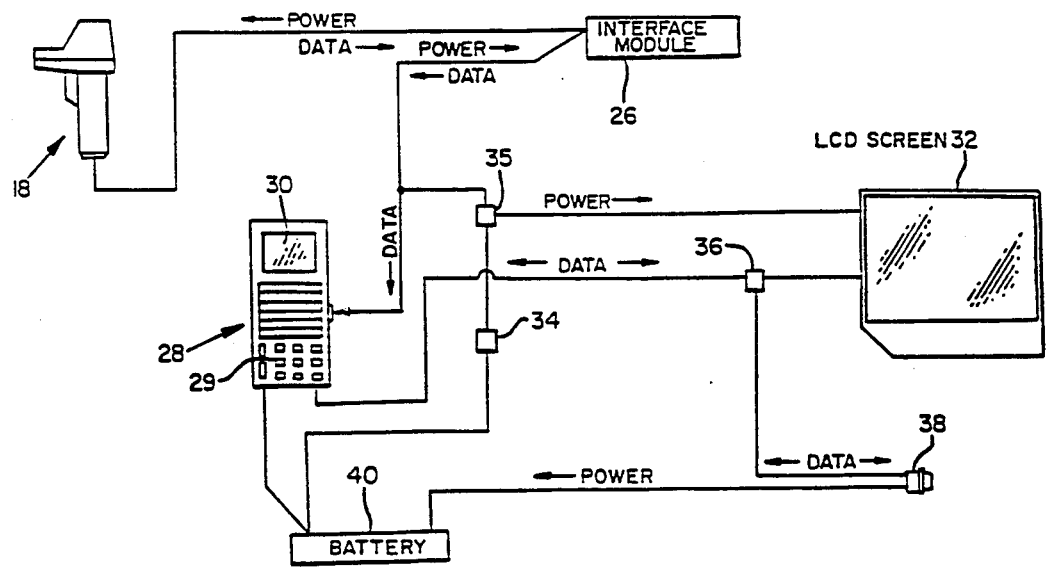
FIG. 2 is a schematic diagram of the portable hospital unit shown in FIG. 1.

FIG. 2 is a schematic diagram showing the elements within the chassis of the unit 16. The scanner 18 is connected via a spring cord to a conventional laser interface module 26 such as MSI Data Corporation Model 1365 for communicating data represented by optical characters to a portable terminal 28. The data terminal 28 is of conventional design such as a PDTIII available from the MSI Data Corporation and includes a microprocessor, associated memory for storing an instruction program and for recording data, a keyboard 29 for data entry, and a display 30 for displaying executing programs and recorded data. The keyboard 29 is reached through the door opening of the unit 16 and is an alternative to the scanner 18 for entering data that is not bar coded, such as the time and date of treatment and the lot number of the animal, or if the scanner malfunctions. Also shown in the schematic is an optional liquid crystal display (LCD) screen 32 connected to the terminal 28 through a reset switch 34, a power switch 35, and a selector switch 36. The reset switch 34 reinitializes the module 26. The switch 35 controls power to the scanner 18 and LCD screen 32 to electrically disconnect them when not required by the operator. The selector switch 36 directs the data that is entered via the scanner 18 into the terminal 28 to either the LCD screen 32 (visible through the transparent door of unit 16 above the menu sheet 24) or to the video monitor 25 via a serial data connector 38 such as an RS232 port. These additional display devices are optionally available because of the difficulty in reading the display 30 from a distance. The LCD screen 32 is normally selected by a single operator while the monitor 25 is usually employed when a crew is working in the hospital 14 and a number of the members must view the display simultaneously. The power source for the unit 16 is a battery 40 which is charged through a power supply line via the connector 38.

Referring to FIG. 3, the treatment data recorded by the unit 16 is periodically transferred to a host computer 50 remote from the animal hospital 14 to update the health histories of observed and treated animals. The host computer 50 is intended for collecting data on feedlot operations in general and maintains the cumulative health history of each animal in the feedlot. The portable unit 16 when transferring the data is coupled to the host computer 50 via a conducting cable 52. The computer 50 in turn is adapted to collect the treatment data recorded within the portable unit 16 and produce an accumulation of such data associated with each animal. This accumulation of data comprises the animal's health history. After the current data is transferred, the computer 50 is programmed to transfer to unit 16 in return the up-to-date health history of each animal as well as current feedlot information, such as newly established lot numbers. The cable 52 also includes the power supply line for charging the battery 40 within the unit 16.

FIG. 4 is a schematic diagram showing the elements comprising the computer 50. The computer itself is of conventional design and includes a video monitor 54 for displaying data and a keyboard 56 for data entry. The computer 50 includes an interface board 58 for receiving data entered via a second bar code scanner 62 and a second laser interface module 64. The interface board 58 transfers the data to and from a central microprocessor 66 equipped with internal memory and disk drives. Data and instruction programs stored in memory and on disk can be viewed on monitor 54. The computer 50 is also connected to a printer 68 for printing the health histories and other related documents. Power is supplied to the computer through a conventional power supply 72. The power supply 72 is also coupled to a battery charger 74 which supplies power for the unit 16. The up-to-date animal health histories, programming, and other feedlot information are transmitted as serial data from the computer 50 along with power to the unit 16 via a connector 76 coupled to the cable 52.

The host computer 50 serves a number of functions in addition to collecting treatment data to produce health histories for each animal treated. One related function is tracking inventory of drugs for treatment of the animals. Referring again to FIG. 4, computer 50 is located adjacent to a drug room 77 which stores drug inventory. Each drug container 78 is labeled with a bar code 79 for identifying the drugs therein with scanner 62. A menu sheet 80 is also present for entering via scanner 62 the amount of drugs within each container when it is removed for drug treatment and the amount remaining in each container when it is returned for restocking or when additional amounts are added to inventory. The computer 50 is programmed to compare the net amount of drugs taken from the inventory as communicated by the scanner 62 against the amount of drugs used in treatment in the animal hospital 14 as communicated by the scanner 18. The difference between the two amounts of drugs over any given time can thereby be determined for monitoring loss due to breakage, theft, etc. This difference, as well as the comparable amounts, are printed at request as a drug usage report as will be described.

The System—Second Embodiment

FIG. 5 shows a second embodiment of the system for possible use where a continuous source of power such as AC power is available in the hospital 14. The system includes a remote "dumb" terminal comprising the scanner 18, the video display 25, and a keyboard 75, all in communication with the host computer 50 through a node 83 that includes communication ports and a power supply. The terminal acts as an extension of host computer 50, relaying treatment data to the computer in real time and displaying the up-to-date health histories transferred to the display from the host computer. This real time communication, when possible, avoids the need for physically moving the portable unit to the host computer and the delay in updating the prior health histories of the animals.

FIG. 5 also shows data entry means such as a transmitter-receiver antenna 85 and indicia means such as transponder 87 attached to an ear for identifying the animal 10. The antenna is preferably of a type similar to an RDREO1, integrater reader available from Allflex International and the tag is preferably a transponder of the type similar to an EID ear tag also available from Allflex International. The antenna is mounted along side the cattle chute 89 and emits a signal that reaches the transponder 87 when animal 10 passes by the antenna 85. The tag 87 in response emits a unique signal identifying the animal, which is electronically "read" by the antenna 85 and communicated to the host computer 50 via a computer interface unit 91 such as a CI-UMO1 from Allflex International. Alternatively, the transponder 87 may be an active transmitter that continuously emits a radio signal for reception by a passive antenna 85. This means for automatically identifying the animal avoids the delay associated with the operator having to move to each animal for identifying it by scanning the ear tag. The entry of treatment data, however, is handled in the same manner as in the first embodiment, with the scanner 18 utilized to scan bar codes on menu sheet 24 corresponding to physical conditions and any drug treatment administered to the animal. The keyboard 75, however, is available if data cannot be entered via the antenna 85 or scanner 18.

Method of Operation

The computer 50 and data terminal 28 within unit 16 are programmed in BASIC, according to the method illustrated in the flowcharts of FIGS. 6 through 8. FIG. 6 shows the options pertinent to the present invention and available to the operator upon logging onto the computer 50. A main menu (81) appears with three options. An inventory menu (82) is selected for working with the drug inventory; a hospital/processing menu (84) is selected for working with the cattle feedlot records; or a third, record keeping menu is selected to use the procedure for monitoring the removal and restocking of drugs as drugs are to be used, such as in the animal hospital 14. With this third option, the operator scans the bar code 79 of the containers 78 that contain drugs required for treatment. He is then prompted to specify the purpose of the drug (86), specify the cattle lots the drug is being used for (88), and to enter the drug amounts removed and restocked (90). This data is used to adjust the book inventory stored within the computer's memory (92). The entry of data is indicated by "carriage returns" (CR).

The inventory menu option (82) is selected for monitoring the inventory. For example, one choice thereunder is to print the daily inventory report, with the book inventory, restocking information, and transactions grouped by product (94). Another option is to manually adjust the inventory in case of a breakage of drugs within the inventory (96). Other options include monitoring the difference between physical inventory as determined by a count and book inventory as determined by the checking in and checking out of drugs previously described. From the inventory menu (82), the operator can also enter the physical inventory for comparison against the book inventory (98). The difference between physical inventory and book inventory of each product (100) can then be presented. The actual physical usage as determined by a physical inventory of the drugs can be compared with the amount administered (102). The totals can then be adjusted as appropriate (104). The operator can additionally print the net amount taken from inventory for drug treatment against the amount recorded from the portable unit 16 (105) as administered.

The third option of the main menu (81), the hospital/processing menu (84), enables the operator to set up new lots for cattle brought into the feedlot and to prepare group drug treatments known as processing orders and hospital treatments which are administered to the animals. Referring now to FIG. 7B, a first option is a lot number menu (106) appearing at the right of the figure and is selected whenever a new cattle lot is to be set up (108). This menu allows the operator to add header information to the lot (110), change the header information (112), or review the lots presently within the feedlot operation (114). The lot menu (106) also includes an option for deleting a cattle lot (116) after the cattle within the lot have been shipped from the feedlot.

A second option under the hospital processing menu is a processing order menu (118). Within this menu is a command for adding a processing order (120). First, a number is assigned to a unique combination of drugs to be administered as the processing order or treatment (122). The drugs desired are then selected (124), and the dosages per head or per 100 pounds are entered (126). The selection of drugs and dosages are then repeated until the processing order is complete (127). The menu (118) also permits the operator to print a list of current processing orders (128) or delete an existing processing order (130). An operator can also view a present processing order (132) and change it if desired (134) by changing the drugs or their amounts (136).

Referring now to FIG. 7A, a third option under the hospital/processing menu (84) is a hospital treatment menu (137). Hospital treatments differ from processing orders in that hospital treatments are normally intended for specific sicknesses and include a combination of drugs for treating that sickness. Processing orders, on the other hand, are not directed to specific sicknesses and are typically administered to all cattle in a lot, outside the animal hospital 14. The hospital treatment menu (137) includes basically the same selections as in the processing order menu (118) and for brevity descriptions of the selections therein are not repeated here.

The other options under the hospital/processing menu (84) include an option (138) at the left of FIG. 7A enabling the operator to assign and record treatments for the animals without entering the data through the portable unit 16. This option minimizes data entry where it is known that all cattle in a given lot will receive a specified treatment. The option (138) includes a command for updating the figures for drugs used in each hospital treatment (140). A similar option (142) allows the operator to assign one or more drugs or processing orders to one or more lots. The operator can print the processing sheet for each order (144) and also has the ability to update figures in the orders for the drugs used (146).

Just as he can assign drugs and treatments to lots, the operator has the option of deleting and editing treatments (148). These options include deleting previously assigned treatments (150), editing existing treatments for a given animal (152), and entering new hospital treatments for a given animal (154).

Communication via cable 52 with the portable unit 16 is also handled through the hospital/processing menu (84). The menu (84) allows the operator to print the daily hospital report (156) of the animals treated as well as receive the day's hospital treatment from the portable (158). The daily treatments are stored on disk in appropriate lot files (160). The operator can also print the day's hospital and processing activity with cost information (162). The updated health history and new lot numbers are then be downloaded into the portable unit 16 to keep it current (164). The program also updates in memory the amount of drugs used in treating each animal (166).

One concern of feedlots is the shipping of cattle not yet suitable for consumption. A further option under the menu (84) allows the operator to check when a lot may be shipped (168) by entering the lot number and estimated shipping date (170). Animals that are not ready for shipping within the lot are then displayed by number (172).

Referring again to FIG. 7B, an operator selects the report/printout menu option (174) whenever a report on treatments administered for each lot is required. Under menu (174), an operator can print a treatment report which indicates all hospital treatments between any two given dates (176). The operator may also print the lot reports which indicate all treatment with drug cost, both processing and hospital, administered to a specified lot since a lot was created (178). A third selection is for summarizing information on each lot by simply printing the header (180).

One other option shown allows the operator under menu (84) to enter the sickness names such as bloat, prolapse, etc., that will be recognized by the portable unit 16 and will appear on menu sheet 24 (186). If the sickness codes are changed at the hospital/processing menu, the menu sheet 24 is also updated.

Figure 8A:
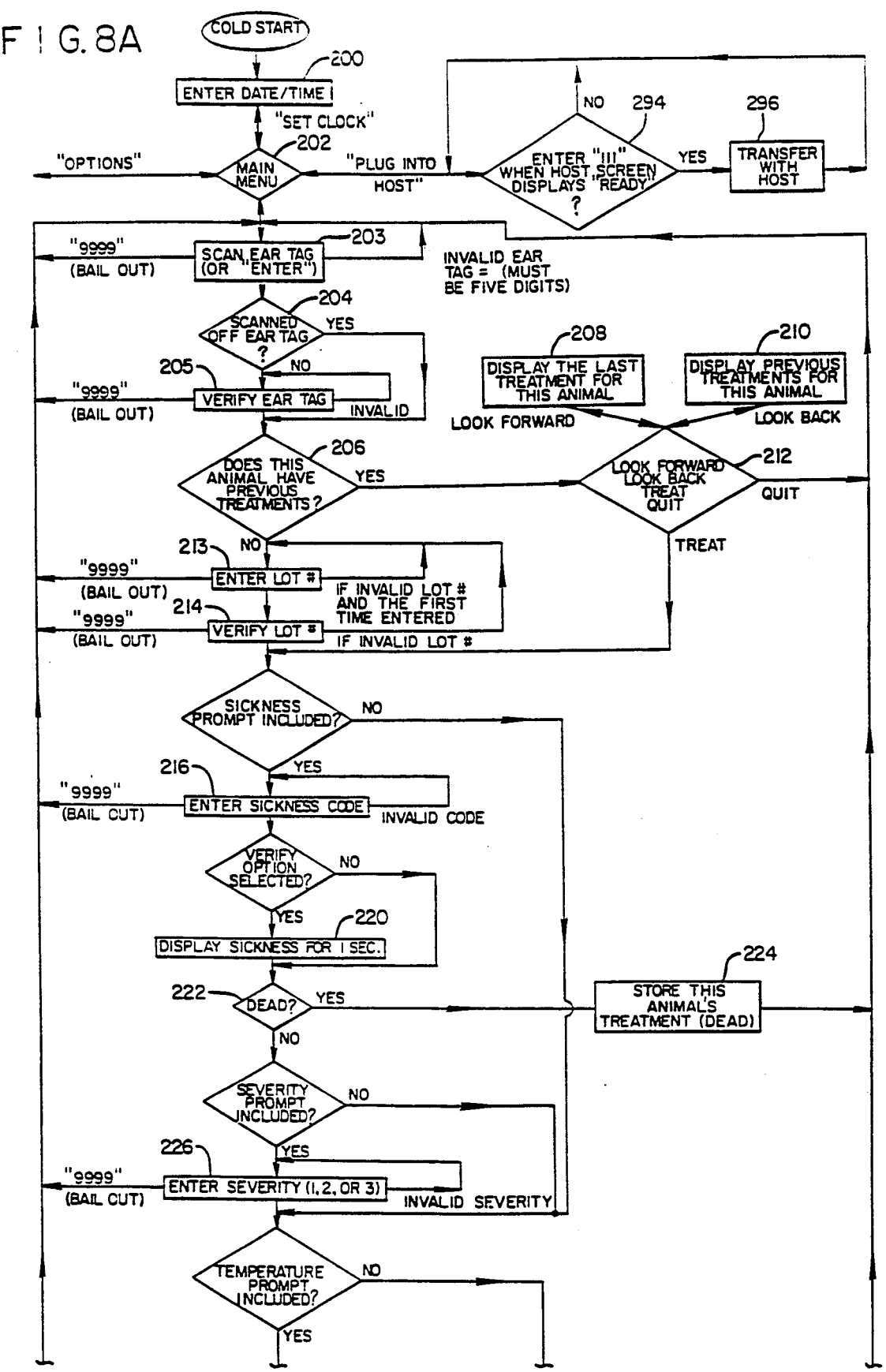
FIG. 8A is a flowchart illustrating a portion of the programming of the portable unit.

The treatment data recorded in the portable unit 16 during a treatment session is entered in response to prompts from the instructional program stored within the terminal 28. FIGS. 8A-8C illustrate the operation of this program. Referring to FIG. 8A, the program prompts the operator 12 on the display such as video monitor 25 to enter the date and time of treatment via the keyboard 29 (200). A main menu (202) then appears on the monitor 25, which gives the operator several choices. One choice allows the operator to include and exclude various prompts and verifications of entered data which appear throughout the figure. Deletion of verifications, shown in these flowcharts, may be made by experienced operators who know the program operation well. The second choice commands the unit 16 to transfer its data to the host computer 50. A third choice allows for the entry of treatment data initially.

The operator thus begins treatment with this third choice by scanning the appropriate number on the menu sheet 24. He is then prompted to scan the ear tag of the animal to be treated or key in the tag number to identify the animal to the unit 16 (203). If he scans the tag, the number is automatically verified (204). If keyed in, the ear tag number is then displayed so that the operator may visually verify his entry (205) before scanning a CR. Once the ear tag has been verified, the program checks to see if the animal is new or has a previous treatment history (206). If the animal does have a record, the monitor 25 displays the last treatment for the animal (208). The operator can then scroll through previous treatments (210) via commands on menu sheet 24 to determine the health history of the animal (212). The operator can also quit the program by scanning the quit command on the menu sheet 24. The quit option is always available throughout the program, though not repeatedly shown in the figure for clarity. All data entered before the quit command is invoked is recorded. On the other hand, the operator can always "bail out" of the program if trouble develops therein by scanning the numerals 9999. No data entered during a treatment session is saved if the operator "bails out."

If no previous treatments have been administered, the operator enters the lot number through keyboard 29 (213) and scans the CR. The program then compares the lot number with those stored in memory. If it is a new lot number, the program alerts the operator that it is included and prompts for reentry. Entering the same number a second time establishes the lot number. The program then prompts the operator to verify his entry (214), which he does by a CR scan.

The operator is then prompted to enter a sickness code (216), such as a respiratory or intestinal condition, appearing on the menu sheet 24. The code is then displayed momentarily for the operator's verification (220). If the sickness code entered indicates the animal is dead (222), this data is stored immediately (224) and the treatment session is ended. If the animal is merely sick, however, the operator is prompted for the severity of the illness and enters a severity code number in response such as 1, 2, or 3 (226) from the menu sheet 24.

Following entry of the animal's identity and sickness diagnosis, the operator may be prompted for other physical conditions such as the animal's temperature. Referring to FIG. 8B, he enters the temperature (232) in response, and it is displayed by the program for operator verification. The last recorded temperature is also displayed (234). The program then prompts the operator for the animal's destination, and the operator enters the pen type and particular pen number by scanning the corresponding numbers on the menu screen 24 (240, 242). These pen types include home pens, recovery pens, or hospital pens such as hospital 14.

Following the intended destination, the operator is prompted to enter numbers identifying the drug or hospital treatment to be administered to the animal (244). Each individual drug and hospital treatment has a unique identification number. If the number entered by the operator is greater than 1000, i.e., has four digits, then the program determines that an individual drug is to be administered (246). The identification number is then checked against a stored list to determine if it is valid (248). The operator is alerted if the number is invalid, and he may attempt reentry (250). Once a valid identification number has been entered, the program checks to determine if the drug requires a withdrawal date (252). Certain drugs require that the animal be kept in the feedlot for a period of time after it is administered a drug to prevent undesired side effects to consumers. The program has stored within it the time period for each drug and calculates from the treatment data the earliest release date of the animal thereafter. If the drug has a withdrawal problem, the information is displayed (254) and the operator is given the opportunity to reconsider administering the drug (256). If no withdrawal date is displayed or if the operator chooses to administer the drug in any event, the program then prompts the operator to enter the number of units to be administered (258). The amount entered is checked against an allowable dosage range to protect the animal from an overdose. The portable unit 16 then verifies the number of units to be administered (260). This drug treatment data is stored within the memory of the terminal 28 for later transfer to the computer 50 (262). The operator is then queried if more treatments are to be given the animal in the present treatment session (264).

Administering and recording hospital treatments are similar to the steps followed for individual drugs. Returning to step (246) and then referring to FIG. 8C, an entered number less than 1000, i.e., two digits, is first verified by the operator as a hospital treatment number (266) via a scanned CR. The program then checks to see if the number entered is a valid treatment number (268). The operator is alerted if the number is invalid (270). If the number is valid, the program then determines if there is a withdrawal problem with this treatment (272) and displays the appropriate information if such problem exists (274). The operator again has the option to proceed or choose another treatment or drug (276). The program also determines whether the treatment has a weight dependent dosage (278). If so, the program prompts the operator to enter the animal's weight (280), which must fall within a predetermined range to be accepted as valid. The entered weight is then verified by the operator (282) via a scanned CR, and the program calculates and displays the dosages to be administered (284). The operator at this point can accept or reject the treatment as calculated (286). If accepted and administered, the amount of treatment is then stored (288).

The operator is then prompted to determine if further drugs or treatment is to be administered to the particular animal (290) in this treatment session. If treatment is finished, all data is then stored within the memory of the terminal 28 and the operator proceeds to examine the next animal. Once treatment is concluded, the operator quits the program (292).

At the conclusion of the day or other predetermined reporting period, the unit 16 is carried to the location of the computer 50 and the two connected by cable 52. Referring again to FIG. 8A, the operator then initiates data transfer via the main menu of the program within the unit 16 (202). The appropriate commands are first selected on the host computer 50 (156-160). The operator then enters a transfer command in response to a prompt (294), and the data is transferred (296). The transferred data is collected to update the health histories of the animals treated in that session. The updated health histories are then transferred back to the terminal 28 for review and display in steps (208) through (212).

Where the "dumb" terminal is employed in place of the portable unit 16, the instructional program illustrated in FIGS. 8A-C is stored within the memory of the host computer 50. No recording of data for later transfer, however, is required.

Having illustrated and described the principles of the invention in a preferred embodiment, it should be apparent to those skilled in the art that the invention can be modified in arrangement and detail without departing from such principles. For example, although the invention is described in the context of a feedlot, it is not so limited. I claim all modifications coming within the spirit and scope of the following claims.

I claim:

1. A method of providing drug treatment to selected individual animals in a livestock feedlot in which groups of animals are normally retained and fed in pens and in which selected individual animals are removed from the pens to a drug treatment location for specific treatments orally or by injection, said method comprising:

identifying an individual animal in need of drug treatment;

moving the identified animal to be treated to the drug treatment location;

entering at the drug treatment location the identity of the animal to be treated;

storing in a computer means in communication with the drug treatment location the sickness and drug treatment history, if any, of the animal to be treated;

in response to entry of the identity of the animal to be treated, providing at the drug treatment location in communication with the computer means, the animal's sickness and drug treatment history, if any;

diagnosing the sickness of the animal to be treated, entering the diagnosed sickness at the drug treatment location, and storing the diagnosed sickness in the computer means as an addition to the animal's sickness history, if any;

evaluating the animal's sickness and drug treatment history and the animal's current sickness, and based on such information, selecting a drug treatment for administration to the animal;

entering the selected drug treatment at the drug treatment location and storing the selected treatment in the computer means as an addition to the animal's drug treatment history, if any;

determining the dosage of each drug to be administered in the selected treatment, and entering the determined dosage at the drug treatment location and storing such dosage in the computer means as an addition to the animal's drug treatment history, if any;

storing in the computer means a drug treatment available for administration and its withdrawal period, if any, and the weight dependency of its dosage, if any;

in response to entry of a selected drug treatment requiring a withdrawal period, calculating in the computer means, for the selected drug treatment, when the animal may be released from the feedlot;

in response to entry of a selected drug treatment the dosage of which is weight-dependent, calculating in the computer means from the entered drug treatment and animal weight, the dosage to be administered, and providing such dosage at the drug treatment location;

and, if desired, obtaining the determined or calculated dosages of the drugs in the selected drug treatment and administering the selected drug treatment to the animal either orally or by injection.

2. The method of claim 1 wherein the animal to be treated is identified and its identity entered at the drug treatment location by a signal generating means affixed to the animal and capable of transmitting an identifying signal to a remote signal sensing means, the method using the signal sensing means to sense the identifying signal from the vicinity of the drug treatment location, converting, if necessary, the sensed identifying signal into a form recognizable by the computer means, and transmitting the recognizable identifying signal from the drug treatment location to the computer means.

3. The method of claim 1 including diagnosing the severity of the sickness, entering the diagnosed severity at the drug treatment location, and storing the entered severity as an addition to the animal's sickness history.

4. The method of claim 1 wherein the identity of the animal is entered at the drug treatment location by keying the identity into a data entry terminal.

5. The method of claim 1 including storing in the computer means drug inventory data for drugs maintained in inventory for use in the available drug treatments including the identification and amount of the drugs in inventory, entering the identification and amount of a drug added to inventory in a computer data entry terminal in communication with the computer means, adding in the computer means the amount of the drug entered in the data entry terminal to the existing stored inventory of the drug to determine a new inventory of the drug, and subtracting in the computer means from the existing stored inventory the amount of a drug used in a selected drug treatment when the dosage of the drug in the selected drug treatment is determined or calculated and entered at the drug treatment location.

6. The method of claim 5 wherein containers of drugs entered into stored inventory are identified by a signal generating means affixed to a container and capable of transmitting to a remote signal sensing means an identifying signal indicative of the drug and the amount of the drug in the container, the method using the signal sensing means to sense a drug and the amount of the drug added to inventory, converting the sensed signal, if necessary, to a form recognizable by the computer means.

7. The method of claim 5 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer means.

8. The method of claim 1 including comparing in the computer means an earliest permitted release date related to a drug withdrawal period with a date the animal is to be shipped from the feedlot.

9. The method of claim 8 including alerting the operator if the release date exceeds the date the animal is to be shipped from the feedlot.

10. The method of claim 8 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

11. The method of claim 1 including storing in said computer means a series of animal sickness conditions and a corresponding recommended drug treatment for a sickness condition; and in response to diagnosing the sickness of the animal to be treated and entering the diagnosed sickness at the drug treatment location, having the computer means select the corresponding recommended drug treatment and transmit the recommended treatment to the drug treatment location.

12. The method of claim 11 including selecting a drug treatment for administration to the animal based on at least the animal's current diagnosed sickness condition, the animal's sickness history and drug treatment history, and the animal's recommended drug treatment;

entering the selected drug treatment at the drug treatment location for storage by the computer means as part of the animal's drug treatment history;

obtaining from a drug inventory the drugs in the dosages necessary for the selected drug treatment from an inventory of drugs at the feedlot;

administering the selected drug treatment to the animal orally or by injection at the drug treatment location.

13. The method of claim 12 including storing in the computer means the drug inventory of drugs available at the feedlot for use in available drug treatments, and subtracting in the computer means the dosage of a drug in a selected drug treatment from the stored inventory of the drug after the selected drug treatment is entered at the drug treatment location.

14. The method of claim 34 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

15. A method of providing drug treatment to selected individual animals in a livestock feedlot in which groups of animals are normally retained and fed in pens and in which selected individual animals are removed from the pens to a drug treatment location for specific treatments orally or by injection, said method comprising:

identifying an individual animal in need of drug treatment;

moving the identified individual animal to be treated to the drug treatment location;

entering at the drug treatment location the identity of the animal to be treated;

storing in a computer communicable with the drug treatment location the sickness history and the drug treatment history, if any, of the animal to be treated, the sickness history including the diagnosed sickness and the drug treatment history including drugs administered in a treatment and the dosage of each drug administered in such treatment;

storing in the computer a list of available drug treatments;

in response to entry of the identity of the animal to be treated, providing at the drug treatment location communicable with the computer means, the animal's sickness history and drug treatment history, if any;

diagnosing the sickness of the animal to be treated;

entering the diagnosed sickness at the drug treatment location;

storing the entered sickness in the computer as an addition to the animal's sickness history, if any;

following entry of the diagnosed sickness, providing at the treatment location a list of available drug treatments;

evaluating the animal's sickness history and drug treatment history and the animal's current sickness, and based on such information and the list of available drug treatments, selecting a drug treatment for administration to the animal;

entering the selected drug treatment at the drug treatment location and storing the selected treatment in the computer as an addition to the animal's drug treatment history, if any;

determining the dosage of each drug to be administered in the selected treatment, and entering the determined dosage at the drug treatment location and storing such dosage in the computer as an addition to the animal's drug treatment history, if any;

if desired, obtaining the determined dosages of the drugs in the selected drug treatment and administering the selected dosages of the drugs in the selected drug treatment to the animal either orally or by injection at the drug treatment location;

storing in the computer the withdrawal period, if any, for drug treatments available for administration and stored in the computer means;

in response to entry of a selected drug treatment requiring a withdrawal period, calculating in the computer, for the drug treatment, when the animal may be released from the feedlot.

16. The method of claim 15 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

17. The method of claim 15 wherein containers of drugs entered into stored inventory are identified by a signal generating means affixed to a container and capable of transmitting to a remote signal sensing means an identifying signal indicative of the drug and the amount of the drug in the container, using the signal sensing means to sense drugs and the amount of a drug added to inventory, converting the sensed signal, if necessary, to a form recognizable by the computer.

18. The method of claim 15 including comparing in the computer an earliest permitted release date related to a withdrawal period with a date the animal is to be shipped from the feedlot.

19. The method of claim 18 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

20. The method of claim 15 including storing in the computer a series of animal sickness conditions and a corresponding recommended drug treatment for a sickness condition; and in response to diagnosing the sickness of the animal to be treated and entering the diagnosed sickness at the drug treatment location, having the computer select the corresponding recommended drug treatment and transmit the recommended treatment to the drug treatment location.

21. The method of claim 20 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

22. The method of claim 36 including storing in the computer drug inventory data for drugs maintained in inventory for use in the available drug treatments including the identification and amount of drugs in inventory, entering the identification and amount of a drug added to inventory into the computer, adding in the computer the amount of the entered drug to the existing stored inventory of the drug to determine a new inventory of the drug, and subtracting in the computer from the existing stored inventory the amount of a drug used in a selected drug treatment when the dosage of the drug in the selected drug treatment is determined or calculated and entered at the drug treatment location.

23. The method of claim 61 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

24. The method of claim 61 wherein containers of drugs entered into stored inventory are identified by a signal generating means affixed to a container and capable of transmitting to a remote signal sensing means an identifying signal indicative of the drug and the amount of the drug in the container, the method using the signal sensing means to sense a drug and the amount of the drug added to inventory and converting the sensed signal, if necessary, to a form recognizable by the computer.

25. A method of providing drug treatment to selected individual animals which are removed from a group of retained animals to a drug treatment location for specific treatments by an operator, the method comprising:

identifying an individual animal in need of drug treatment;

moving the identified animal to be treated to the drug treatment location;

entering the animal's identity into a computer system;

in response to entry of the animal's identity, providing the animal's health and drug treatment history, if any, to assist the operator in making a diagnosis;

diagnosing the health condition of the identified animal and entering the diagnosed condition into the computer system as an addition to the animal's health history, if any;

evaluating the animal's health and drug treatment history and the animal's diagnosed condition, and based on such information and the operator's judgment, selecting a drug treatment for the animal;

entering the selected drug treatment into the computer system as an addition to the animal's drug treatment history, if any;

determining the dosage of each drug in the selected treatment and entering such dosage into the computer system as an addition to the animal's drug treatment history, if any;

in response to entry of a selected drug treatment requiring a withdrawal period, calculating in the computer system, for the selected drug treatment, when the animal may be released; and in response to entry of a selected drug treatment whose dosage is weight-dependent, if any, calculating in the computer system, from the animal's weight and selected drug treatment, a dosage for the animal.

26. The method of claim 25 wherein the entering steps are performed with a data terminal and the providing and calculating steps are performed with a computer.

27. The method of claim 25 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer system.

28. The method of claim 25 including diagnosing the severity of the animal's condition and entering the diagnosed severity for recording as an addition to the animal's health history.

29. The method of claim 25 including comparing in the computer an earliest permitted release date related to a drug withdrawal period with a date the animal is to be shipped.

30. The method of claim 29 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer system.

31. The method of claim 25 including:

storing in the computer system the identification and amount of drugs in inventory for use in drug treatment;

entering into the computer system the identification and amount of a drug added to inventory;

adding the amount of the identified drug to the existing inventory; and subtracting the amount of a drug used in a selected drug treatment from the existing inventory.

32. The method of claim 31 wherein a container of a drug entered into inventory includes a signal generator for transmitting to a signal sensor an identifying signal indicative of the drug and the amount of the drug in the container.

33. The method of claim 31 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

34. The method of claim 25 including:

storing in the computer system a series of animal health conditions and a corresponding recommended drug treatment for at least some of the health conditions; and in response to diagnosing the condition of the identified animal and the entering of the diagnosed condition, communicating the corresponding recommended drug treatment to the operator at the drug treatment location.

35. The method of claim 34 including:

selecting a drug treatment for the animal based on at least the animal's current diagnosed condition, the animal's health and drug treatment history, and the animal's recommended drug treatment; and entering the selected drug treatment into the computer system as an addition to the animal's drug treatment history.

36. The method of claim 35 including:

storing in the computer system the inventory of drugs available for use in drug treatments; and subtracting the dosage of a drug used in the selected drug treatment from the inventory of the drug after the drug treatment is entered.

37. The method of claim 35 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

38. A method of providing drug treatment to selected individual animals which are removed from a group of retained animals to a drug treatment location for specific treatments by an operator, the method comprising:

moving a selected individual animal to be treated to the drug treatment location;

entering into a computer the animal's identity;

in response to entry of the animal's identity, providing the animal's health and drug treatment history, if any, to assist the operator in making a diagnosis;

diagnosing the condition of the animal to be treated;

entering into the computer the diagnosed condition as an addition to the animal's health history, if any;

following entry of the diagnosed condition, providing a list at the drug treatment location of available drug treatments;

evaluating the animal's health and drug treatment history and the animal's diagnosed condition and, based on such information, the operator's judgment and the list of available drug treatments, selecting a drug treatment for the animal; and in response to selection of a drug treatment requiring a withdrawal period, calculating in the computer system, for the selected drug treatment, when the animal may be released.

39. The method of claim 38 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

40. The method of claim 38 wherein containers of drugs entered into stored inventory are identified by a container a signal generating means capable of transmitting to a remote signal sensing means an identifying signal indicative of the drug and the amount of the drug in the container, using the signal sensing means to sense drugs and the amount of a drug added to inventory, converting the sensed signal, if necessary, to a form recognizable by the computer.

41. The method of claim 38 including comparing in the computer an earliest permitted release date related to a drug withdrawal period with a date the animal is to be shipped.

42. The method of claim 41 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

43. The method of claim 38 including storing in the computer a series of animal sickness conditions and a corresponding recommended drug treatment for a sickness condition; and in response to diagnosing the sickness of the animal to be treated and entering the diagnosed sickness at the drug treatment location, having the computer select the corresponding recommended drug treatment and transmit the recommended treatment to the drug treatment location.

44. The method of claim 43 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

45. The method of claim 38 including storing in the computer drug inventory data for drugs maintained in inventory for use in the available drug treatments including the identification and amount of the drugs in inventory, entering the identification and amount of a drug added to inventory into the computer, adding in the computer the amount of the entered drug to the existing stored inventory of the drug to determine a new inventory of the drug, and subtracting in the computer from the existing stored inventory the amount of a drug used in a selected drug treatment when the dosage of the drug in the selected drug treatment is determined or calculated and entered at the drug treatment location.

46. The method of claim 45 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

47. The method of claim 45 wherein containers of drugs entered into stored inventory are identified by a signal generating means affixed to a container and capable of transmitting to a remote signal sensing means an identifying signal indicative of the drug and the amount of the drug in the container, the method using the signal sensing means to sense drugs and the amount of a drug added to inventory, and converting the sensed signal, if necessary, to a form recognizable by the computer.

48. A system for providing drug treatment to selected individual animals which are removed from a group of retained animals to a drug treatment location for specific treatment by an operator, comprising:

(a) a computer for:

providing a health and drug treatment history, if any, for an animal to be treated;

providing a record of drug treatments available for administration and their withdrawal periods, and the weight dependency of their dosages, if any;

calculating, from an entered drug treatment requiring a withdrawal period and from treatment data, when an animal may be released; and calculating, from an entered drug treatment whose dosage is weight-dependent and from an animal's weight, a dosage for an animal;

(b) a data terminal at the treatment location and in communication with the computer, the data terminal operable for:

entering the identity of an animal to be treated;

providing the identified animal's health and drug treatment history from the computer to the operator to assist in making a diagnosis, if any;

permitting entry by the operator of a diagnosis of the identified animal, the diagnosis added to the animal's health history; and permitting entry by the operator of a drug treatment for the identified animal, the drug treatment added to the animal's drug treatment history.

49. The system of claim 48 including:

a signal generating means affixed to an animal for transmitting an animal identifying signal; and a remote sensing means near the drug treatment location for sensing the identifying signal and communicating the identifying signal to the computer.

50. The system of claim 48 wherein the drugs are stored in containers and the system further includes:

a signal generating means affixed to a container for transmitting to a remote signal sensing means an identifying signal indicative of the drug and the amount of the drug in the container; and signal sensing means for sensing the identifying signal and converting it, if necessary, to a form recognizable by the computer.

51. The system of claim 48 including comparing in the computer an earliest permitted release date related to a drug withdrawal period with a date the animal is to be shipped.

52. The method of claim 51 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

53. The system of claim 48 including storing in the computer a series of animal sickness conditions and a corresponding recommended drug treatment for a sickness condition; and in response to diagnosing the sickness of the animal to be treated and entering the diagnosed sickness at the drug treatment location, having the computer select the corresponding recommended drug treatment and transmit the recommended treatment to the drug treatment location.

54. The method of claim 53 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

55. The system of claim 48 including a data entry terminal for entering the identification and amount of drugs added to a drug inventory, the computer further adapted for:

storing data in the drug inventory data for use in the available drug treatments, the data including the identification and amount of the drugs in inventory;

adding the amount of the drugs entered to the existing stored inventory of the drug to determine a new inventory of the drug; and subtracting from the existing stored inventory the amount of a drug used in a selected drug treatment when the dosage of the drug in the selected drug treatment is determined or calculated and entered at the drug treatment location.

56. The system of claim 55 including:

a signal generating means affixed to an animal for transmitting an animal identifying signal; and a remote sensing means near the drug treatment location for sensing the identifying signal and communicating the identifying signal to the computer.

57. The system of claim 55 wherein the drugs are stored in containers and the system further includes:

a signal generating means affixed to a container for transmitting to a remote signal sensing means an identifying signal indicative of the drug and the amount of the drug in the container; and signal sensing means for sensing the identifying signal and converting it, if necessary, to a form recognizable by the computer.

58. An animal treatment system located at a treatment location for providing and updating drug treatment and health histories of animals to an operator, comprising:

a computer programmed for receiving and storing information regarding drug treatment and health histories of animals and, for selected drug treatment requiring a withdrawal period, calculating, for the selected drug treatment, when an animal may be released;

data entry means at the treatment location for entering into the computer animal identification, drug treatment administered by the operator and health conditions of an animal observed by the operator; and data output means at the treatment location and coupled to the computer for providing to the operator, in response to entry of the identity of the animal, the animal's drug treatment and health histories, if any, an operator thereby being able to obtain at the treatment location an animal's drug treatment and health histories before administering further drug treatment and to update instantly the animal's drug treatment history based on the treatment administered to the animal and the animal's health history based on the animal's observed physical condition.

59. The animal treatment system of claim 58 wherein the computer is located at the treatment location.

60. The animal treatment system of claim 58 wherein the data entry means comprises a bar code scanner.

61. The animal treatment system of claim 58 wherein the data entry means comprises a keyboard.

62. The animal treatment system of claim 58 wherein the data entry means comprises an antenna and transponder attached to the animal for identifying the animal.

63. The system of claim 58 including:

a signal generating means affixed to an animal for transmitting an animal identifying signal; and a remote sensing means near the drug treatment location for sensing the identifying signal and communicating the identifying signal to the computer.

64. The system of claim 58 including comparing in the computer an earliest permitted release date related to a drug withdrawal period with a date the animal is to be shipped.

65. The method of claim 64 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

66. The system of claim 58 including storing in the computer a series of animal sickness conditions and a corresponding recommended drug treatment for a sickness condition; and in response to diagnosing the sickness of the animal to be treated and entering the diagnosed sickness at the drug treatment location, having the computer select the corresponding recommended drug treatment and transmit the recommended treatment to the drug treatment location.

67. The method of claim 66 wherein the animal to be treated is identified and its identity entered at the drug treatment location by a signal generating means affixed to the animal for transmitting an identifying signal to a remote sensing means near the drug treatment location, the sensing means for sensing the identifying signal and communicating the identifying signal to the computer.

68. The system of claim 58 including a data entry terminal for entering the identification and amount of drugs added to a drug inventory, the computer further adapted for:

storing data in the drug inventory data for use in the available drug treatments, the data including the identification and amount of the drugs in inventory;

adding the amount of the drugs entered to the existing stored inventory of the drug to determine a new inventory of the drug; and subtracting from the existing stored inventory the amount of a drug used in a selected drug treatment when the dosage of the drug in the selected drug treatment is determined or calculated and entered at the drug treatment location.

69. The system of claim 68 including:

a signal generating means affixed to an animal for transmitting an animal identifying signal; and a remote sensing means near the drug treatment location for sensing the identifying signal and communicating the identifying signal to the computer.

70. The system of claim 68 wherein the drugs are stored in containers and the system further includes:

a signal generating means affixed to a container for transmitting to a remote signal sensing means an identifying signal indicative of the drug and the amount of the drug in the container; and signal sensing means for sensing the identifying signal and converting it, if necessary, to a form recognizable by the computer.

* * * * *

UNITED STATES PATENT AND TRADEMARK OFFICE
CERTIFICATE OF CORRECTION

PATENT NO. : 5,315,505
DATED : May 27, 1994
INVENTOR(S) : William C. Pratt et al.

It is certified that error appears in the above-identified patent and that said Letters Patent is hereby corrected as shown below:

Column 13, line 42, after "The method of claim" delete "34" and insert --13--.

Column 19, line 45, change "The method" to --The system--.

Column 19, line 62, change "The method" to --The system--.

Signed and Sealed this

Seventh Day of May, 1996

Attest:

BRUCE LEHMAN

Attesting Officer      Commissioner of Patents and Trademarks